United States Patent [19]
Brown et al.

[11] Patent Number: 4,950,245
[45] Date of Patent: Aug. 21, 1990

[54] MULTIPLE FLUID CARTRIDGE AND PUMP

[75] Inventors: Eric W. Brown, Newport Beach; Charles Kienholz, San Dimas; Steve Busak, Laguna Niguel, all of Calif.

[73] Assignee: I-Flow Corporation, Irvine, Calif.

[21] Appl. No.: 216,512

[22] Filed: Jul. 8, 1988

[51] Int. Cl.⁵ .............................................. A61M 5/00
[52] U.S. Cl. ...................................... 604/153; 604/67; 604/246; 128/DIG. 12
[58] Field of Search ............... 604/65, 67, 118, 120, 604/131, 151, 153, 154, 246, 250, 410; 128/DIG. 12

[56] References Cited

U.S. PATENT DOCUMENTS

| | | | |
|---|---|---|---|
| 2,351,828 | 1/1942 | Marsh | 417/44 |
| 4,094,318 | 6/1978 | Burke et al. | |
| 4,142,524 | 3/1979 | Jassawalla et al. | |
| 4,199,307 | 4/1980 | Jassawalla | 417/474 |
| 4,273,121 | 6/1981 | Jassawalla | 604/153 |
| 4,340,153 | 7/1982 | Spivey | |
| 4,397,639 | 8/1983 | Eschweiler et al. | |
| 4,479,797 | 10/1984 | Kobayashi et al. | |
| 4,497,370 | 1/1985 | Beard et al. | |
| 4,498,843 | 2/1985 | Schneider et al. | 417/22 |
| 4,563,175 | 1/1986 | LaFond | |
| 4,601,700 | 7/1986 | Thompson et al. | 604/65 |
| 4,650,469 | 3/1987 | Berg et al. | 604/131 |
| 4,653,987 | 3/1987 | Tsuji et al. | |
| 4,657,490 | 4/1987 | Abbott | |
| 4,666,430 | 5/1987 | Brown et al. | 604/141 |
| 4,673,390 | 6/1987 | Archibald | |
| 4,696,671 | 9/1987 | Epstein et al. | |
| 4,705,506 | 11/1987 | Archibald | |
| 4,718,467 | 1/1988 | Di Gianfilippo et al. | |
| 4,725,205 | 2/1988 | Cannon et al. | |
| 4,728,265 | 3/1988 | Cannon | |
| 4,731,057 | 3/1988 | Tanaka et al. | |
| 4,734,092 | 3/1988 | Millerd | |
| 4,741,736 | 5/1988 | Brown | 604/134 |
| 4,756,706 | 7/1988 | Kerns et al. | 604/66 |
| 4,850,972 | 7/1989 | Schulman et al. | 604/151 |
| 4,865,584 | 9/1989 | Epstein et al. | 604/67 |

FOREIGN PATENT DOCUMENTS 3500467 7/1986 Fed. Rep. of Germany ........ 604/65

Primary Examiner—John D. Yasko
Assistant Examiner—Adam J. Cermak
Attorney, Agent, or Firm—Robert M. Asher

[57] ABSTRACT

A pump housing which contains a plurality of linear peristaltic pumps and receives a fluid source cartridge. The cartridge is provided with retaining knobs for engaging retaining holes in the front end of the pump housing. A cartridge further contains a tab at its rear end for engaging a locking mechanism in the pump housing. The cartridge contains linear fluid conduits which align with the linear peristaltic pumps for pumping fluid from the fluid source pouches within the cartridge. Each pump is individually controlled by a programmable controller within the pump.

4 Claims, 5 Drawing Sheets

MULTIPLE FLUID CARTRIDGE AND PUMP

BACKGROUND OF THE INVENTION

This invention relates to a multiple fluid cartridge which is insertable into a programmable infusion pump.

It is an object of this invention to provide a compact, lightweight infusion pump which may be used for ambulatory patients. It is a further object of this invention to provide a pump which can be conveniently used with fluid source cartridges.

There has been a demonstrated need for pumps which can intravenously administer a plurality of drug solutions. For example, multiple drug chemotherapy treatments have been used to treat diseases such as cancer. Many of the drugs used in chemotherapy and other therapies cannot be mixed together prior to an infusion. Some of these drugs react to neutralize one another. Other drugs react to form precipitates which may block the catheter tube, or possibly cause an embolism in the patient.

Pumps have been developed which can concurrently pump a plurality of fluids through a multilumen catheter into a patient. The multilumen catheter keeps the drugs separate until they reach the bloodstream. For example, in U.S. Pat. No. 4,741,736 (Brown), a pump is disclosed which uses a roller to push fluid out of a plurality of compartments in an infusion pump. The different fluids in each of the compartment is pumped out at the same time by the action of the single roller In infusion pump patent, U.S. Pat. No. 4,666,430 (Brown and Tai), a multiple syringe pump is disclosed in which a canister of compressed gas serves as the power source for pumping fluid out of a syringe. All of the syringes are controlled by the same canister of gas, and variation in the pumping rate of a syringe is controlled by valves on the outlets of the syringes.

An object of the present invention is to provide in a single ambulatory housing, separately controlled pumping mechanisms for each of a plurality of fluid sources. It is a still further object of the present invention to provide multiple fluid source cartridges which are attachable to a pump of the present invention.

SUMMARY OF THE INVENTION

The present invention is directed to an infusion pump system including a fluid source cartridge which is attachable to a pump housing. The pump housing has a plurality of linear peristaltic pumps. Each fluid source in the cartridge has a linear fluid conduit which aligns with a peristaltic pump when the cartridge is inserted into the housing. The pumping of fluid from any of the fluid sources in the cartridge is controlled by the source's respective peristaltic pump.

The infusion pump housing may be advantageously provided with a programmable controller to permit individual control over each of the peristaltic pumps. This permits operating the pumps sequentially or concurrently and at any selected pumping rate.

The multiple fluid source cartridge may be further provided with a module containing a plurality of plunger members. Each module overlies a linear conduit and the plunger members are alternately moved by the fingers of the peristaltic pump in the pump housing to cause fluid to be pumped from its respective fluid source. The same cartridge may be used for any number from one to four fluid sources, it being only necessary to provide the appropriate number of plunger modules in the cartridge.

Other objects and advantages of the present invention will become apparent during the following description of the presently preferred embodiment of the invention taken in conjunction with the drawings.

DETAILED DESCRIPTION OF THE DRAWINGS

DETAILED DESCRIPTION OF THE PREFERRED EMBODIMENTS

Figure 1:
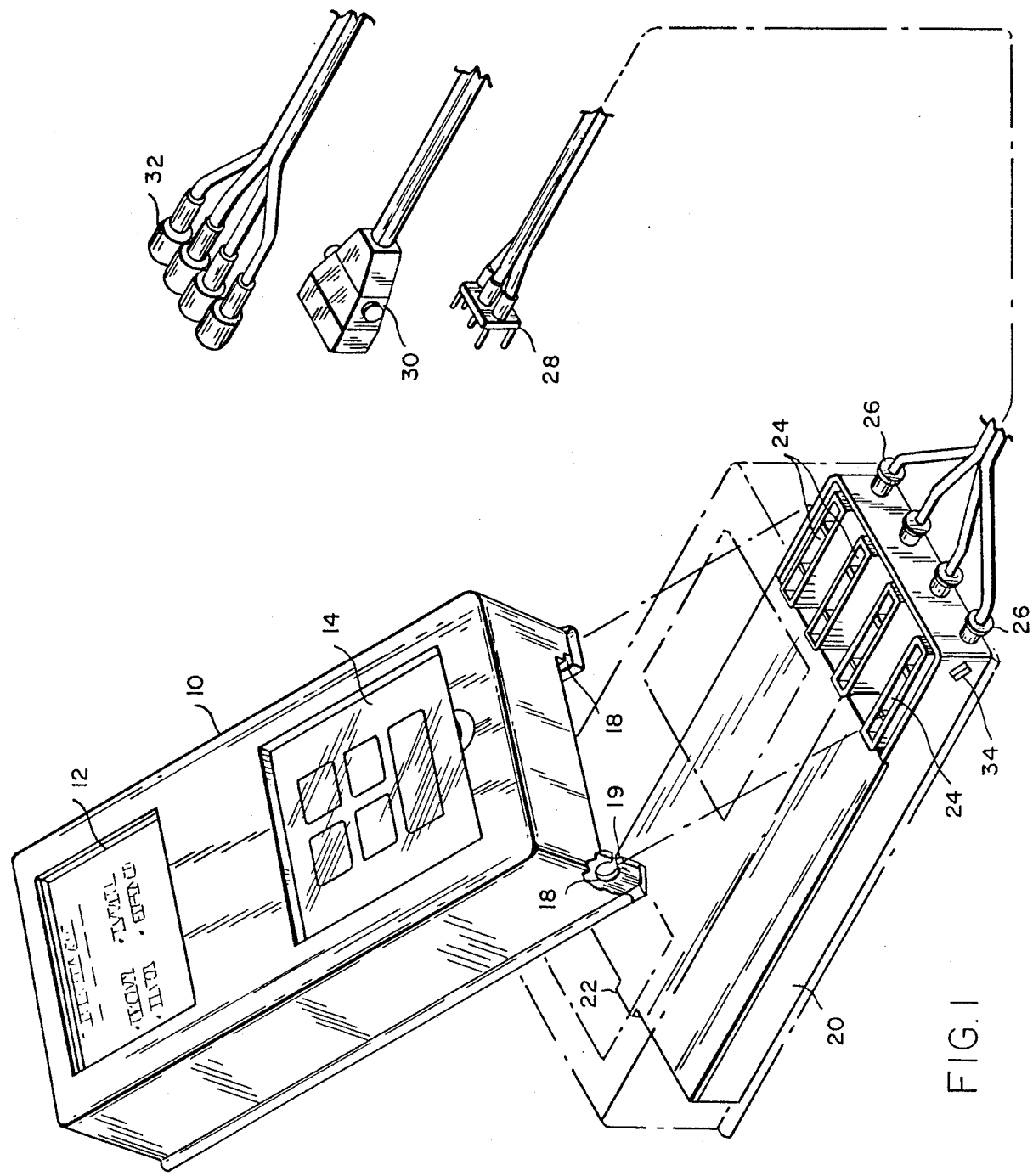
FIG. 1 is a perspective view of the pump and cartridge of the present invention.
Figure 5:
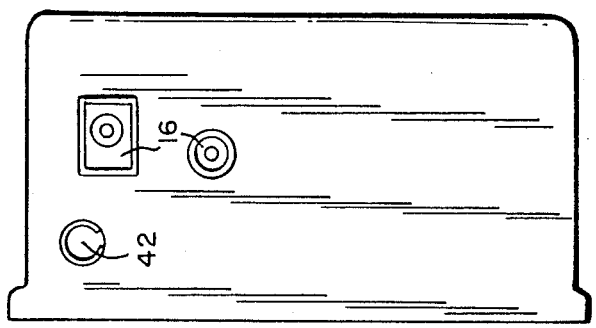
FIG. 5 is an end view of the pump of FIG. 4.

Referring now to FIG. 1, a pump housing 10 is provided for pumping fluid from a multiple fluid cartridge 20. The pump housing 10 is provided with a liquid crystal display 12, a keyboard 14 and as shown in FIG. 5, programming jacks 16. The underside of the pump housing 10 forms a cavity for receiving the cartridge 20. The cavity extends through one end of the pump housing 10. Just inside the open end of the housing, there are two cartridge retaining holes 18 for engaging retaining knobs 34 on the cartridge.

The cartridge 20 houses one or more fluid sources 44. The cartridge 20 further has space for four plunger modules 24. Each plunger module 24 has three plunger members which are used for pumping fluid through a linear fluid conduit positioned directly beneath the module 24. The inside end of the fluid conduit connects to one of the fluid sources in the body of the cartridge 20. At the outer end of the linear fluid conduit a connector 26 serves as the output port for delivering fluid into an output lumen.

In FIG. 1, all four lumens are being used by the cartridge 20. The lumens are fused together to form a multi-lumen tube for outputting the fluid to a connector for making connection with an implanted catheter, for example. The multi-lumen output tube may be connected to any of a variety of a multi-lumen connectors. Three possibilities are shown in FIG. 1. A needle connector 28 may be used in which each lumen is connected to a hollow injection needle. The needle connector may be inserted through a silicone block to make connection with a connector for a multi-lumen catheter. Another option is a multi-lumen connector such as that described in co-pending U.S. patent application Ser. No. 178,673 filed on Apr. 7, 1988, owned by the same assignee as the present invention. The disclosure of said application is hereby incorporated by reference herein. A third possibility for the output tube is to connect each lumen separately to a luer connector 32 so that individual connections can be made to four separate catheter lines.

Figure 2:
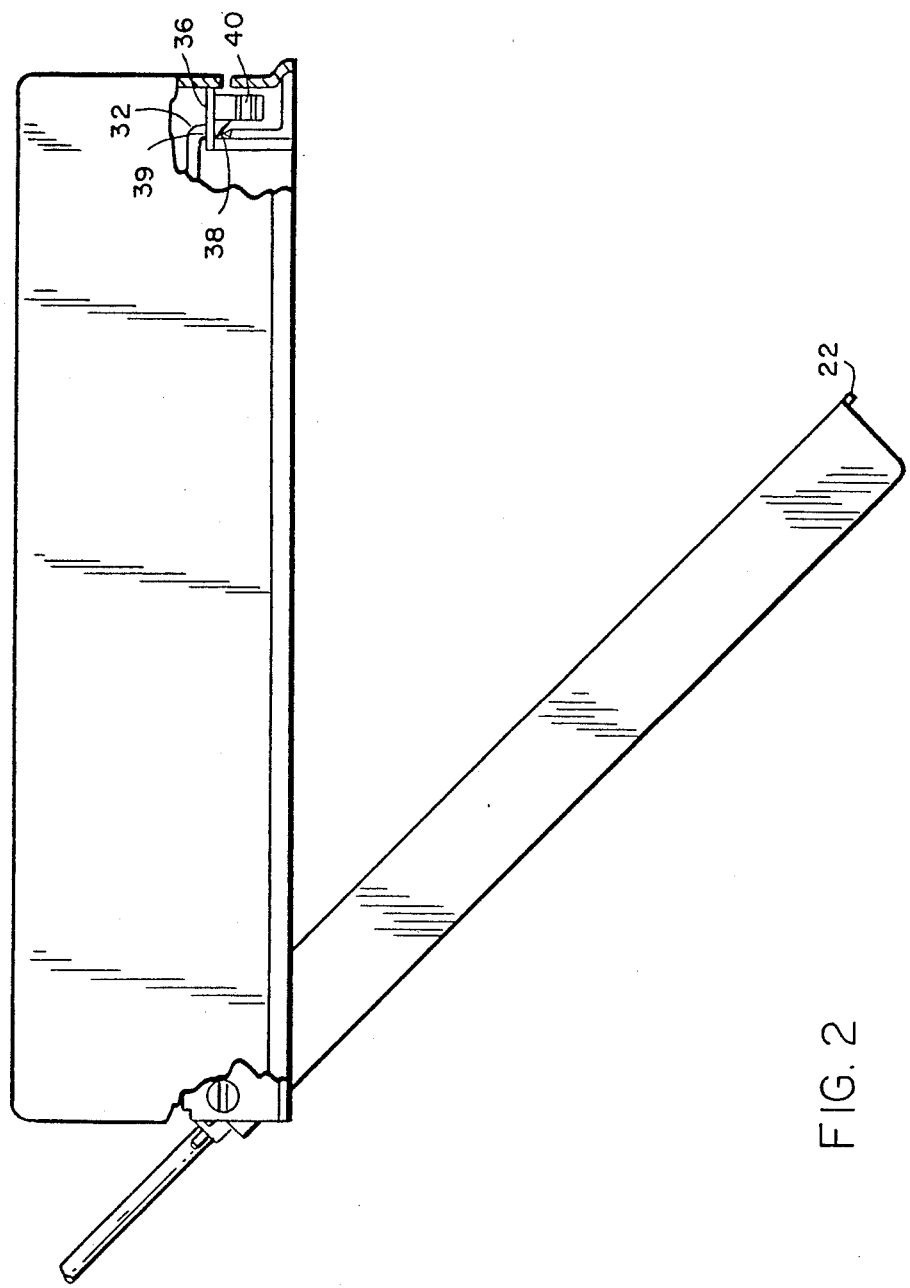
FIG. 2 is a side view illustrating how a cartridge attaches to a pump according to the present invention.

The cartridge 20 is provided with a retaining knob 34 on two opposite sides near its front end. The retaining knob 34 is preferably a linear flange cocked at an angle with respect to the bottom of the cartridge. Preferably, the knob 34 is cocked at approximately a 45 degree angle with respect to the bottom of the cartridge, one end of the knob pointing towards the top of the cartridge and the other end of the knob pointing towards the front end of the cartridge. This permits the end of the knob 34 which points towards the top of the cartridge to be inserted into the retaining hole 18 in the pump housing 10 while the rear of the cartridge 20 hangs below the pump as shown in FIG. 2. The retaining hole 18 has an entrance opening 19 at the front of the housing. Once the entire knob 34 has been inserted through the opening 19 into the retaining hole 18, the cartridge 20 can be swung upwards to fully engage the pump housing 10.

At the rear of the pump housing 10, a lock 36 is provided for engaging a tab 22 on the rear end of the cartridge. The lock 36 according to the presently preferred embodiment is provided with a beveled edge 38 and a retaining edge 39. A spring 40 urges the lock 36 to hold the cartridge in place. As the cartridge 20 is pushed up into the housing, the cartridge tab 22 slides along the beveled edge 38 and pushes the lock back against the action of the spring 40. Once the tab 22 gets above the retaining edge 39, the spring forces the lock back beneath the cartridge tab 22 so that the tab 22 is held up on top of the retaining edge 39. Thus, the lock 36 prevents the cartridge 20 from falling out of the pump housing. At the front of the cartridge, the retaining knob 34 which entered the retaining holes 18 in a horizontal position are at an angle when the cartridge is fully inserted. Thus, the retaining knobs 34 cannot slide out of the retaining holes 18.

Figure 4:
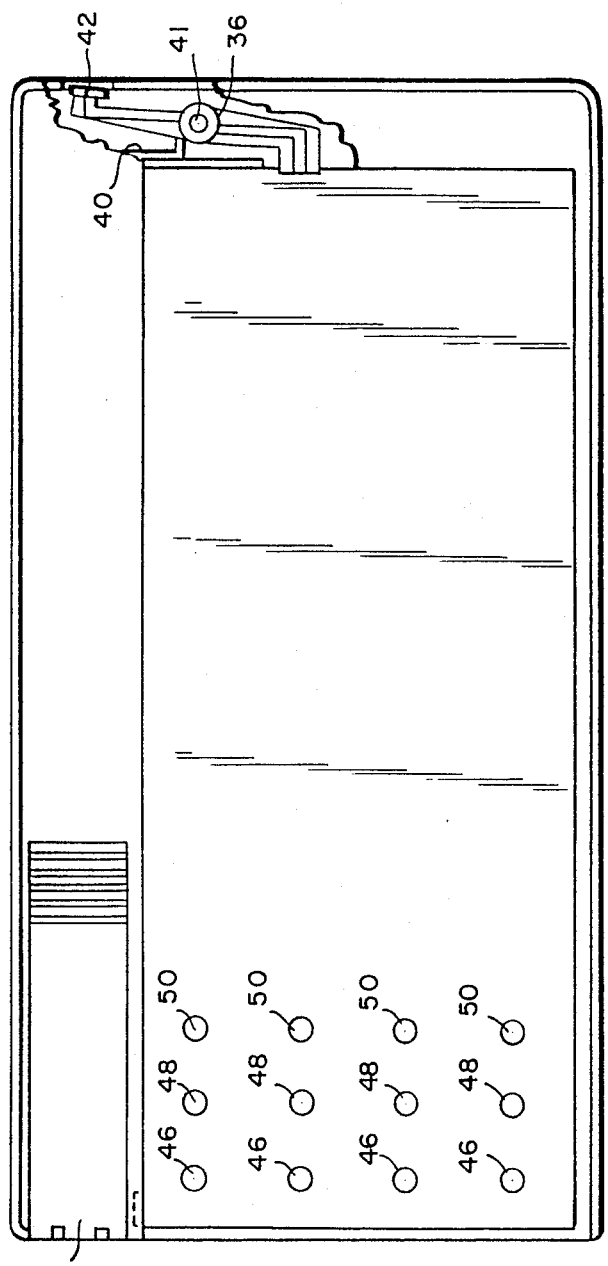
FIG. 4 is a bottom plan view of the pump of the present invention without a cartridge in place.

The cartridge lock 36 of the pump housing is further shown in FIG. 4, where it can be seen that the lock 36 swivels about an axis 41. The spring 40 urges the engaging end of the lock 36 against the cartridge 20. A cartridge can be released from the pump housing 10 by pushing against the other end of the lock 36 which forms a button 42 through an opening in the pump housing. When button 42 is pressed, the lock 36 swings away from the cartridge 20, permitting the tab 22 to disengage from the retaining edge 39 of the lock. Thus, the back end of the cartridge can fall out of the pump housing and when the retaining knobs 34 are in horizontal position with respect to the pump housing, they may be slid out through the openings 19.

Figure 3:
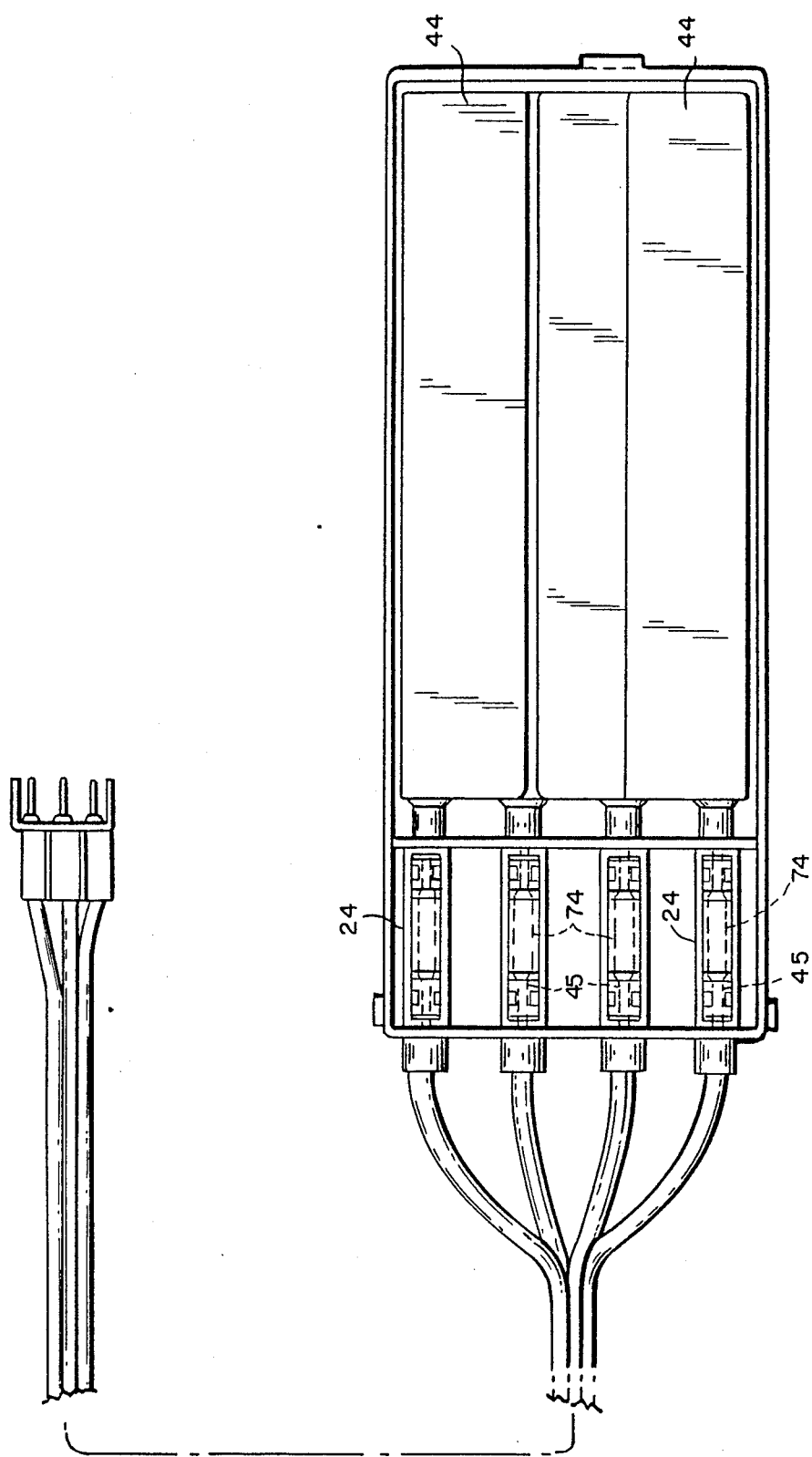
FIG. 3 is a plan view of a cartridge of the present invention with the top wall of the cartridge housing removed.

FIG. 3 reveals the fluid sources stored within the cartridge 20. Each fluid source 44 is provided with a linear fluid conduit 45 beneath a plunger module 24. The fluid sources 44 are flexible pouches. The presently suggested procedure for using the cartridges 20 is to provide them with empty pouches. The desired fluid is injected into the connector port 26, using a syringe or other conventional means. After filling the pouch 44 with the desired amount of fluid, the connector port 26 is attached to the output tube. When all of the pouches are filled with their fluid, the cartridge may be inserted into the pump housing 10 and a purge cycle may be run on each of the fluid sources to pump out all of the air which may have gotten into the pouch or conduit line. After purging the air, the cartridge 20 is ready for use in an infusion.

Figure 6:
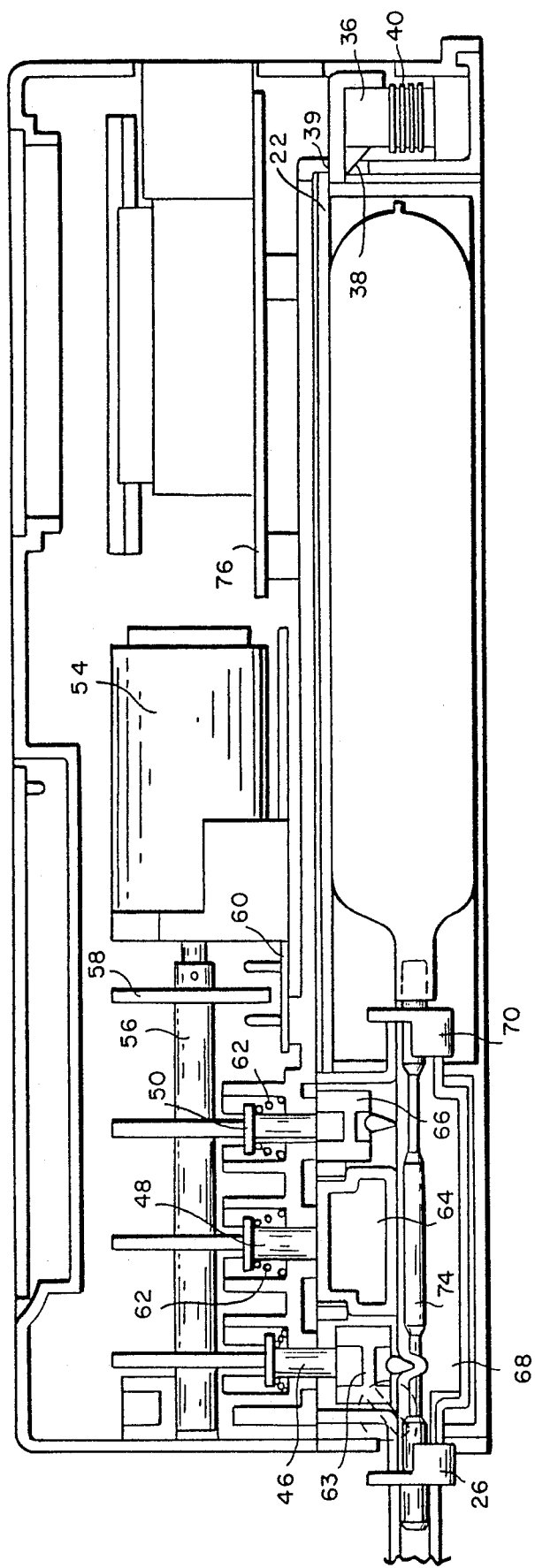
FIG. 6 is a side cross-sectional view of the pump and cartridge of the present invention.

Referring now to FIGS. 4 and 6, the pump of the present invention is provided with a plurality, four in this case, of linear peristaltic pumps. Linear peristaltic pumps are well known and any conventional design may be used to accomplish the objectives of the present invention. The pump of the preferred embodiment is a three finger pump, called such because the three cams which are repeatedly lowered and raised to provide the desired pumping action. Each pump thus activates three cam followers, including an output cam follower 46 and a pump cam follower 48 and an input cam follower 50. Power for the pumps is provided by a battery which may be loaded into a cavity behind a battery cover 52 alongside the peristaltic pumps within the housing 10. Each pump is provided with its own motor 54 which turns a cam shaft 56. The cam shaft 56 is provided with a timing disk 58. The timing disk is read by a timing circuit on a printed circuit board 60. Signal feedback from the timing circuit on the printed circuit board 60 can be provided to control the speed of the motor 54 and thus control the rate of fluid infusion from any of the fluid sources. A spring 62 is located about each of the cam followers to urge the cam follower into a retracted position.

The cam followers interact with the plungers of the plunger module 24. Each plunger module 24 includes an output valve 63, a pump 64 and an input valve 66. The linear fluid conduit 45 beneath each plunger assembly 24 is provided through a silicone block 68. A silicone block 68 is provided in each of the plunger modules. A connector 70 at the end of the fluid conduit within the cartridge 20 is used for attaching the conduit to its respective fluid source 44. Each linear conduit 45 has an enlarged portion beneath the pump plunger 64. This enlarged portion of the conduit is called a pump tube 74.

Pumping is performed as follows. With the pump plunger 64 and the input valve 66 retracted, the output cam follower 46 is lowered against the output valve 63 to close off the fluid conduits. This permits the pump tube 74 to fill with fluid. Next, the input valve 66 is lowered by the input cam follower 50 to close off the pump tube 74 and prevent fluid from flowing back into the fluid source 44. The output cam follower 46 is then retracted permitting the output valve 63 to open. The pump plunger 64 is activated by the pump cam follower 48 to push fluid out through the conduit and into the output tube. Then the output valve 63 is again closed by the output cam follower 46. The pump cam follower 48 and the input cam follower 50 are retracted to permit the pump plunger 64 and the input valve 66 to open, thereby permitting the pump tube to refill with fluid. Thus, fluid is pumped out of the fluid source pouch 44. The rate of pumping is controlled by the speed of the motor 54 which is monitored by the timing printed circuit board 60.

A programmable microprocessor is provided on a control circuit board 76. Each of the four pump motors is controlled by the controller board 76. Since each fluid source has its own pump and pump motor, the rate and sequence of fluid infusion is entirely flexible. Infusions may take place concurrently or sequentially and at any rate. The desired sequence and rates of infusion are programmed into the controller board 76 through the programming jacks 16. Thus, in accordance with the present invention, multiple fluid infusion treatments may be delivered to a patient in any number of sequences and rates with an ambulatory pump. Thus, the pump of the present invention provides physicians with the great latitude for selecting multiple-fluid drug regimens for treating patient illnesses.

It is further noted that by swinging the cartridges into the cartridge receiving space of the pump housing, rather than sliding the cartridge into that space, the present invention allows for a cam follower to be in the lowered position. In such a position, the cam follower would block a cartridge from being slid into its space. However, when the cartridge is swung into position, the extended cam follower merely pushes up against its corresponding plunger member.

Of course, it should be understood that various changes and modifications to the prefered embodiment described above will be apparent to those skilled in the art. For example, any number of fluid sources may be provided in a cartridge. Also, if a pump ensured that all the cam followers were retracted, the cartridge could be inserted by sliding it into place. These and other changes can be made without departing from the spirit and scope of the invention and without diminishing its attendant advantages. It is therefore intended that such changes and modifications be covered by the following claims.

I claim:
1. A multiple fluid source cartridge comprising;
   a rigid housing;
   a plurality of fluid containing compartments located within said housing;
   a linear conduit connected to each one of said fluid containing compartments;
   a plurality of plunger members superposed on each of said linear conduits; and
   an output port accessible from outside said housing for each of said linear fluid conduits.
2. The cartride of claim 1 further comprising a detachable module for housing each plurality of plunger members.
3. The cartridge of claim 1 wherein said output port for each of said linear fluid conduits connects to a multilumen catheter.
4. The cartridge of claim 1 wherein said fluid containing compartments comprise flexible pouches.

* * * * *